United States Patent [19]

Schnepp-Pesch et al.

[11] Patent Number: 4,817,631
[45] Date of Patent: Apr. 4, 1989

[54] METHOD FOR REMOVING TISSUE FROM A BODY

[76] Inventors: Wolfram Schnepp-Pesch, Schönblick 6, D-7505 Ettlingen; Josef Lindenberg, Käthe-Kollwitz-Str. 10 a, D-7500 Karlsruhe 41; Dieter Köhler, Auf'm Kampe 56, 5948 Schmallenberg-Winkhausen, all of Fed. Rep. of Germany

[21] Appl. No.: 126,474
[22] Filed: Nov. 30, 1987

Related U.S. Application Data

[63] Continuation of Ser. No. 19,797, filed as PCT EP86/00020 on Jan. 21, 1986, published as WO86/06951 on Dec. 4, 1986, abandoned.

[30] Foreign Application Priority Data

May 23, 1985 [DE] Fed. Rep. of Germany ....... 3518547

[51] Int. Cl.$^4$ ............................................. A61B 10/00
[52] U.S. Cl. ................................... 128/753; 128/749; 128/764; 604/167
[58] Field of Search ............................... 128/751–755, 128/749, 764, 765; 604/164–170

[56] References Cited

U.S. PATENT DOCUMENTS

| 3,097,646 | 7/1963 | Scislowicz | 604/167 |
| 3,313,299 | 4/1967 | Spademan | 604/167 |
| 3,540,447 | 11/1970 | Howe | 604/165 |
| 4,256,119 | 3/1981 | Gauthier | 604/165 |
| 4,338,934 | 7/1982 | Spademan | 604/167 |
| 4,664,128 | 3/1987 | Lee | 128/753 |
| 4,697,600 | 10/1987 | Cardenas et al. | 128/753 |

FOREIGN PATENT DOCUMENTS 2139004  2/1973  Fed. Rep. of Germany ...... 604/167

Primary Examiner—Dalton L. Truluck
Assistant Examiner—Denise Whelton
Attorney, Agent, or Firm—Antonelli, Terry & Wands

[57] ABSTRACT

A cannula as part of a biopsy instrument set is provided, which has a mandrin guided in the cannula and a seal arranged in the interior of cannula for ease of handling to ensure that a clearly defined tissue or tissue fluid quantity is removed from the interior of a body.

13 Claims, 2 Drawing Sheets

METHOD FOR REMOVING TISSUE FROM A BODY

This is a continuation of application Ser. No. 019,797 filed as PCT EP86/00020 on Jan. 21, 1986, published as WO86/06951 on Dec. 4, 1986, now abandoned.

The invention relates to a method and apparatus for removing liquids, tissue or the like from the interior of a body, such as a living organism, with an elongated hollow body, such as a hose or a cannula and with a suction device.

For example biopsy instrument sets with a cannula as the hollow body are knwon, which at the end to be inserted in the body is ground in an appropriate manner and, at least during insertion or piercing, a mandrin is provided in the cannula. The mandrin can be pointed in stiletto-like manner at its front distal end and is also referred to as a stiletto. At its rear, proximal end, it can have a handle. When the distal end has come into the area where the tissue sample is to be taken, the mandrin is at least partly or even completely drawn out of the cannula and a tissue sample is removed for histological and/or cytological examination by further piercing or pressureless cutting, a medical syringe being fixed for additional suction of the bioptate after inserting the steel needle and subsequently removing the mandrin. The syringe is then drawn up, the complete arrangement rotated in order to cut out a cylinder of material and finally the arrangement is drawn out of the body. The cylinder of material is ejected from the cannula by pressing down the syringe. The procedure described for removal purposes can easily lead to a displacement of the cannula, which can lead to misrouting with complications and can also cause pain. Until the medical syringe is drawn up, the end, which e.g. in the case of pneumocentesis is inserted in the lung, is disadvantageously linked with the outside air. This biopsy instrument set does not permit the removal of tissue fluid. For this purpose it is necessary to provide another biopsy instrument set in which the cannula is fixed to the cylinder of a medical syringe and a hollow stiletto guided in the cannula is fixed to the syringe plunger so that, on drawing up the syringe, tissue fluid is sucked through the resulting vacuum into the syringe cylinder. This syringe suffers from the disadvantage that, due to the considerable volume produced in the cylinder by the suction, it is necessary to remove a relatively large amount of tissue fluid and this can lead to the traumatization of the examined tissue. However, due to the relatively large initial volume, prior to suction and at the start of suction, there can be a relatively weak vacuum, which can be disadvantageous. The latter applies with respect to the sucking of liquid from wounds, effusions, body cavities or the like by means of hoses, such as catheter hoses and medical syringes.

An object of the present invention is to develop an improved apparatus of the aforementioned type that by means thereof and in a clearly defined, careful manner, it is possible to provide a method or removing tissue or fluid in a simple and in particular easily manageable manner, in such a way that removal takes place efficiently and requires less time, while being less of a strain for the patient. In addition, through a smaller number of manipulations, the traumatization risk is reduced and the accuracy at removal points improved.

According to the invention, the above object is achieved by an apparatus of the present type in that in the hollow body is guided an elongated obturator substantially adapted to the cavity thereof and a seal is arranged in an area of the hollow body remote from the insertion end. Tissue samples for histological examination, tissue fluid for cytological examination and other fluids are drawn up and received with a high suction power in the case of the apparatus used according to the invention into the cavity freed in the hollow body on drawing up the obturator. While the apparatus according to the invention is particularly intended for biopsies on living organisms, it can also be used for postmortem biopsies and for taking samples from any appropriate dead material, as well as for material testing purposes. The procedure required according to the invention is much simpler. After inserting the elongated hollow body with the obturator inserted therein into the body, the obturator is drawn up and, optionally, completely removed. In the latter case the seal is constructed in self-sealing manner, so that following the removal of the obturator it provides a complete seal and consequently the vacuum in the hollow body is maintained. Thus, any fluid drawn up is maintained in the hollow body and can be removed therewith from the body. In the case of puncturing for tissue removal purposes by means of a cannula with an introduced mandrin, the latter is drawn up and, optionally, completely removed, so that once again the vacuum produced is maintained. The cannula merely needs to be inserted over the length of the desired tissue plug and turning for cutting is not longer necessary, the cutting being brought about during the easy insertion as a result of vacuum action. On pulling the cannula out of the body, the tissue sample is ejected from the cannula by again inserting the mandrin. It is much easier to keep the tissue samples, no matter what their consistency, e.g. whether they are lung, kidney or liver tissues. This results from the fact that when removing a tissue sample on cutting or piercing the tissue plug from the tissue area to be examined, the taking up of the tissue is aided by the vacuum in the cannula and the tissue plug cut from the tissue is sucked into the cannula, so that there is no compression thereof. A disadvantageous traumatization of the bioptate is obviated, because the cut-out cylinder of tissue cannot shoot into a syringe. Due to the fact that the seal is located at a distance from the cannula end introduced into the body and preferably in the vicinity of the remote end, but in the interior thereof and optionally in the interior of a widened attachment or the like, the advantage is obtained that after withdrawing the mandrin and also when removing tissue fluid, a clearly defined quantity thereof can be sucked into the freed area of the cannula at a higher vacuum than in the prior art and is then flexibly absorbed upstream of the seal by the air cushion resulting from the residualforce prior to the drawing up of the obturator. This clearly defined small quantity, but which is adequate for examination purposes, does not lead to excessive traumatization of the tissue removed. Thus, when the cannula according to the invention is used, it causes less stress for the patient. As a result of the inventive construction, the performance and yield of the autopsy (namely a longer intact tissue cylinder) are improved as a result of the easy handling thereof. It has surprisingly been found that the inventive apparatus has a much higher suction pressure at the distal end of the hollow body than when using conventional medical syringes for producing the vacuum. This is doubtless due to the fact that as a result of the normally tightly fitting obturator in the hollow body (the obturator and the hollow body being matched to one another with limited tolerances), the ratio of the residual volume containing residual air prior to drawing up the obturator to the suction volume obtained on drawing up the obturator is very small, or the reciprocal value is high.

As a result of the seal no material can be sucked, because even after removing the mandrin, the hollow channel can be closed again. Unlike in the prior art, a medical syringe is no longer necessary. A better aiming precision and greater sensitivity is obtained, e.g. on insertion, but also when turning the cannula for turning cutting purposes. In particular, all manner of cutting operations at the distal end of the cannula can be combined with the construction according to the invention.

According to a preferred embodiment, the seal is made from rubber, silicone or some other material. The seal is preferably inserted as a completely closed sealing disk in the interior of the hollow body and is then pierced by the mandrin, so that the seal completely surrounds the latter in a reliable sealing manner. The seal necessarily remains tight on partial drawing out or removal of the obturator. If the obturator or mandrin is to be completely removed, the sealing disk remains completely tight due to self-sealing when the mandrin is completely removed and therefore seals the needle cavity again in a complete manner and consequently maintains the vacuum causing the suction action in the hollow body. According to a preferred embodiment, the hollow body has a widened cavity, e.g. in the interior of an adapter, such as a Luer adapter and the seal is formed in the widened cavity. With such a construction it is easier to insert the seal. This leads to the further advantage that the larger the diameter of the seal is than the mandrin pierced through it, more sealing compound is available, so as to again achieve a reliable seal on completely removing the mandrin. Advantageously, the seal is secured by a retaining ring or by bonding. Apart from the aforementioned advantages on inserting and using the cannula according to the invention, the fact that no medical syringe has to be used for drawing up the mandrin or stiletto and should not be used for the optimum utilization of all the advantages of the invention, results in the further advantage of material saving and, therefore, lower price. The inventive apparatus can, in particular, be used with an endoscope and can, if necessary, be correspondingly constructed. In place of the rigid bend of the conventional endoscope, the apparatus can have an angular, adequately flexible and axial, but rigid guide hose for insertion through the endoscope. The hose is preferably constructed as a metallic hose with a rigid front, i.e. distal, sharpened end, i.e. formed as a cannula, whose length, as a function of its diameter, is determined by the endoscope bend dimensions. The metallic hose can e.g. be formed by a helical spring or in some other way. If necessary, in order to ensure the necessary vacuum in the removal region, it is internally provided with a ring packing at the transition point between the flexible hose and the rigid cannula. A marking or a stop can be provided at the proximal actuating end for checking the drawing up length.

Further advantages and features of the invention can be gathered from the claims and following description relative to a non-limitative embodiment of the invention and with reference to the drawings, wherein:

FIG. 5b shows a larger-scale detail of FIG. 5a.

Figure 1:
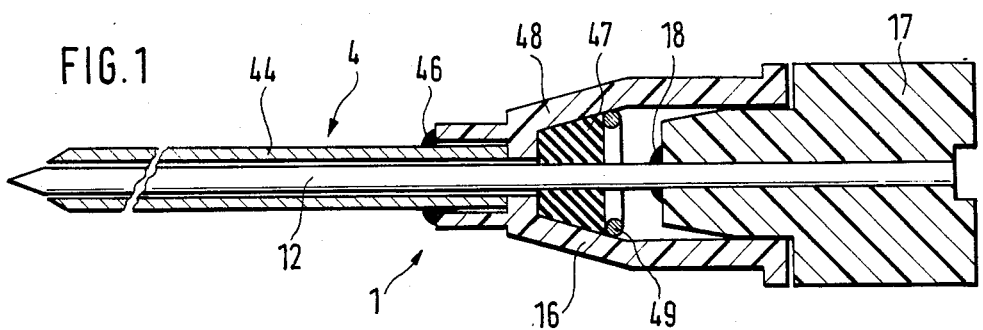
FIG. 1 shows a first embodiment of a biopsy instrument set with a preferred embodiment of the inventive cannula.

The biopsy instrument set 1 shown in FIG. 1 has a cannula 4, which comprises a metal shank 44 and a grip 16, in which the metal shank 44 is fixed and joined e.g. by means of a sealing compound 46. Grip 16 is made from a suitable stable plastic and can, e.g., be constructed in the form of an adapter, such as a Luer adapter. However, even in the embodiment shown in FIG. 1 it still has the function of a grip and can be used in the embodiment shown in FIGS. 2 to 4. The grip 16 could obviously also have a different configuration from that shown in FIG. 1 and could, e.g., be provided with radially projecting flanges and the like. The biopsy instrument set 1 also has a stiletto or mandrin 12, which is guided in cannula 4. Cannula 4 and mandrin 12 are pointed and sharpened at their end remote from grip 16 and, e.g., cannula 4 has a trocar ground section, inner ground section or the like. At its proximal end, mandrin 12 has a handle 17, which in the same way as grip 16 can be made from stable plastic and is preferably made from the same plastic, is fixed to the mandrin by use of e.g., a sealing compound 18. When the mandrin 12 is fully inserted in cannula 4, the tip of the mandrin 12 projects out of the cannula end to be introduced into the body. A seal 47 is placed in grip 16 of cannula 4. It rests on the one hand on a shoulder 48 formed on the interior of grip 16 and is also secured on its side remote from shoulder 14 by an inserted ring 49, which is secured, e.g., by welding to grip 16. Seal 47 is preferably a disk made from a suitable elastic material, such as plastic, natural rubber, artificial rubber, e.g., silicone rubber or the like. On inserting mandrin 12 in cannula 4, the sealing disk 47 is perforated and then surrounds the mandrin 12 with extremely high tightness. Even when mandrin 12 is drawn out, the sealing disk seals itself again in its perforated area, so that it also remains completely tight.

The biopsy instrument set is used for removing, from body organs, tissue which is in particular to be examined histologically and the cannula 4 with inserted mandrin 12 (i.e., in the reprsentation according to FIG. 1) is introduced into the interior of the body, optionally with the aid of a guide needle, such as a Straus cannula. While firmly holding cannula 4 by its grip 16, for removal purposes mandrin 12 is drawn up after acting on its handle 17 and consequently the front cavity of cannula 4 is freed for receiving tissue, which has already been sucked to a certain extent into the distal end of cannula 4. In particular, mandrin 12 can be completely removed, seal 47 then automatically and reliably sealing the inner area of cannula 4. When taking up tissue and, in particular in the case of a suitable ground joint of the inserted end of the cannula, the latter is moved by rotation or pressing on grip 16 and is pressed further in the area which is of interest, which leads to a screwing movement of cannula 4 and consequently a tissue plug is cut out in bioptate form from the tissue and is sucked up completely into cannula 4. Cannula 4 with the bioptate is drawn out of the body and, by means of mandrin 12 which has been reinserted in cannula 4, the bioptate is removed from the cannula and is placed, e.g., in formalin for fixing purposes.

In fundamentally the same manner as described relative to FIG. 1, the biopsy instrument set with the cannula 4 according to the invention can also be used for withdrawing by suction a clearly defined quantity of tissue fluid for cytological examination, without any medical syringe being necessary, although such a syringe can be used, as will be shown hereinafter. In this case there is no cutting out of tissue parts by the cannula and with the latter firmly held, tissue fluid is sucked into the cannula 4 merely by drawing up mandrin 12 by means of handle 17, it being possible to very accurately determine the quantity by the amount of drawing. Hereinafter a description is given of another biopsy instrument set construction with fundamentally the same embodiment of the inventive cannula and fundamentally identical parts are given the same reference numerals.

Figure 2:
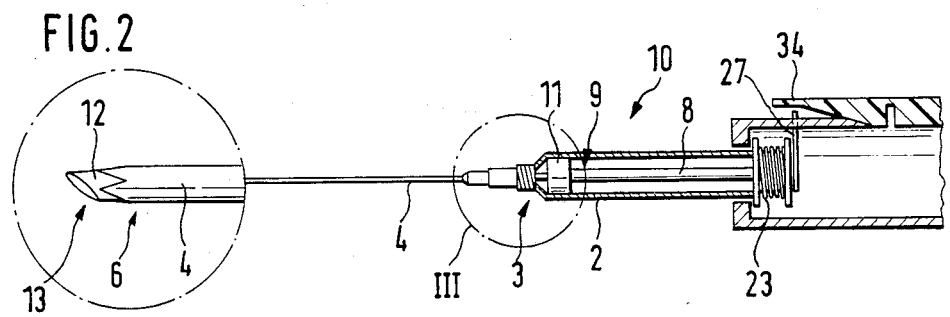
FIG. 2 shows a general view of another biopsy instrument set with the preferred embodiment of the inventive cannula.
Figure 3:
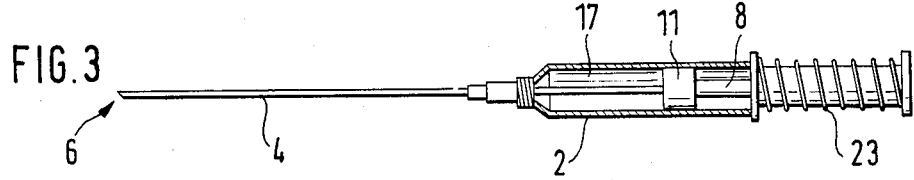
FIG. 3 shows a partial representation of FIG. 2 with the plunger withdrawn.
Figure 4:
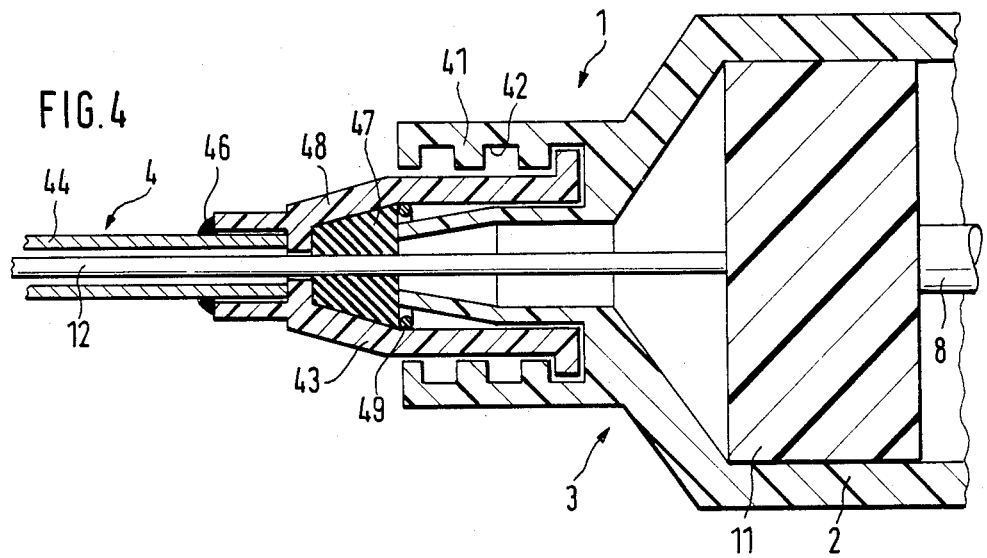
FIG. 4 shows a detail of area III in FIG. 2, completely in section.

The biopsy instrument set 10 shown in FIGS. 2 to 4 has a medical syringe with a hollow cylinder 2 to which the cannula 4 is connected at a front end 3. End 3 of hollow cylinder 2 can have a joining shoulder 41 with an internal thread 42, to which the cannula 4 can be fixed by means of an adapter 43, e.g., a Luer adapter and can fundamentally be constructed in the same way as grip 16 of FIG. 1, but in this case is not used as such. A plunger 8 is guided in hollow cylinder 2 and is provided at its end facing cannula 4 with a piston 11 located in the hollow cylinder. A stiletto or mandrin 12 guided in cannula 4 is joined to the plunger 8. At their ends 6, 13 remote from hollow cylinder 2 or plunger 8, cannula 4 and mandrin 12 are pointed and sharpened, e.g., the cannula 4 with a trocar ground joint, inner ground joint or the like. With the plunger 8 fully inserted into the hollow cylinder 2, the tip of the mandrin 12 projects a few millimeters out of the end 6 of cannula 4. Plunger 8 can either be manually drawn up in hollow cylinder 2 or can be under the tension of a spring 23 and can initially be secured by an arresting means 27 connected to hollow cylinder 2 and which can be released by an actuator 34, as shown in FIG. 1.

As stated, cannula 4 has an adapter 43, which is fixed to the metal shank 44 of cannula 4, e.g., by means of a sealing compound 46. As described relative to FIG. 1, a seal 47 is inserted in adapter 43 of cannula 4. The seal is constructed and secured in the same way as described relative to FIG. 1.

This biopsy instrument set is also used for removing, from body organs, tissue which is to be examined histologically or tissue fluid which is to be examined cytologically. It is used fundamentally in the manner described relative to FIG. 1 by gripping on cylinder 2 and plunger 8 or by drawing up the plunger by releasing a tensioned spring.

Figure 5A:
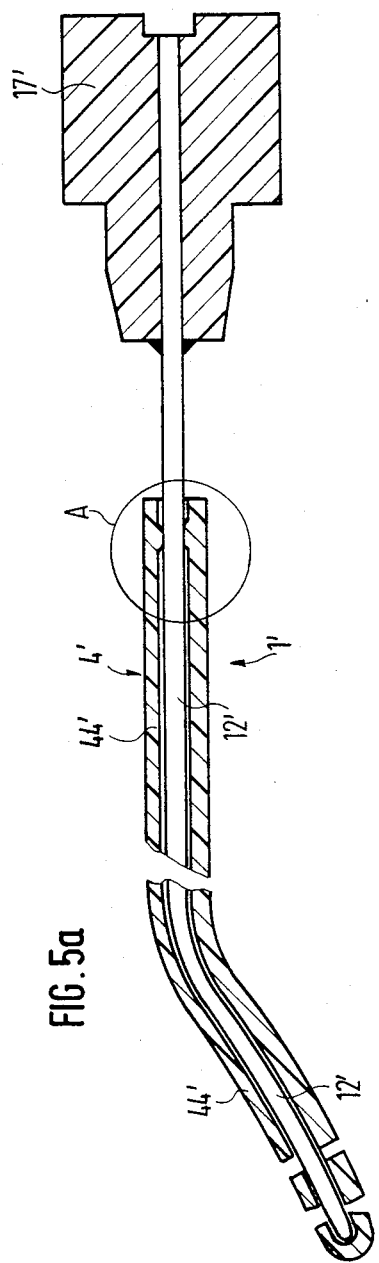
FIG. 5a shows a suction tube constructed according to the invention.
Figure 5B:
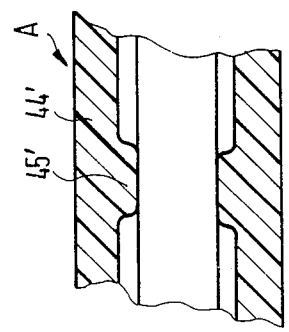

FIGS. 5a and 5b, the apparatus 1' according to the invention is shown with a suction tube 4' and a hollow plastic body 44'. In the manner described with reference to FIG. 1, the seal can be formed in the cavity of an adapter at the end remote from the end of the tube to be inserted in the body. An obturator 12', e.g., also a mandrin having a grip 17' at one end, is inserted in the hollow body 44'. The end of tube 4' to be inserted in the body and which is opposite to the insertion opening of obturator 12' is closed in the represented embodiment, while suction openings are provided in this area in the side wall. As a function of the intended use, this could be replaced by having the end wall open. In the represented embodiment, sealing takes place in the manner represented in detail A in FIG. 5b, in that the tube wall 44' has an annular thickened portion 45' in its inner circumference and the cross-section left free by said thickened portion 45' when mandrin 12' is not inserted has a smaller diameter than the latter. By inserting the mandrin 12', the thickened portion is forced outwards, so that a reliable seal is obtained. By appropriate defined compression, during heat treatment or the like, thickened portion 45' can be formed from the plastic body 44' of the tube or in any other appropriate manner.

We claim:

1. A method of removing tissue from an interior of a body, comprising:
    inserting an elongated obturator, a first end of which comprises a point, into a cavity of an elongated hollow body, wherein said obturator is adapted to fit tightly in a hollow space of said hollow body, and wherein said hollow body includes a sharpened insertion end and a self-sealing seal in an area remote from said insertion end, which completely seals said hollow body, and wherein said obturator is inserted through said seal, thereby perforating said seal such that said first end of said obturator is directed towards said insertion end of said hollow body, wherein before said obturator is inserted through said seal, said seal contains no perforations, and wherein said seal is capable of maintaining a vacuum within said hollow body upon complete withdrawal of said obturator out of said hollow body;
    inserting said hollow body housing said obturator into said interior of said body;
    drawing said obturator up such that said first end of said obturator is directed away from said insertion end of said hollow body, wherein said tissue is cut away by said sharpened insertion end and drawn up within said cavity of said hollow body and said obturator from said interior of said body.

2. A method according to claim 1, wherein said body is a living organism.

3. A method as in any of claims 1 and 2, wherein said seal is made from rubber.

4. A method as in any one of claims 1 and 2, wherein said seal is made from plastic.

5. A method according to claim 3, wherein said seal is made from silicone.

6. A method as in any one of claims 1 and 2, wherein the step of drawing said obturator includes drawing said obturator completely out of said hollow body, and wherein said seal maintains a vacuum within said hollow body.

7. A method according to claim 6, further comprising following the step of removing said hollow body from said interior of said body, reinserting said obturator into said hollow body, wherein said tissue, is ejected from said hollow body.

8. A method as in any one of claims 1 and 2, wherein said seal is secured in said hollow body by a retaining ring.

9. A method as in any one of claims 1 and 2, wherein said seal is secured in said hollow body by an annular welding point.

10. A method according to claim 1, further comprising rotating said hollow body about a longitudinal axis while pressing said insertion end into the tissue to be removed, thereby cutting said tissue by said sharpened insertion end.

11. A method according to claim 2, wherein said tissue is selected from the group consisting of lung tissue, kidney tissue and liver tissue.

12. A method according to claim 1, wherein said sharpened insertion end comprises a trocar ground section.

13. A method according to claim 1, wherein said sharpened insertion end comprises an inner ground section.

* * * * *